(12) United States Patent
Schilling et al.

(10) Patent No.: US 9,406,129 B2
(45) Date of Patent: Aug. 2, 2016

(54) METHOD AND SYSTEM FOR RANKING INSTRUMENTS

(71) Applicant: MEDTRONIC, INC., Minneapolis, MN (US)

(72) Inventors: Eric A. Schilling, Ham Lake, MN (US); Nancy M. Germanson, Maple Grove, MN (US); Manfred Justen, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 139 days.

(21) Appl. No.: 14/254,288

(22) Filed: Apr. 16, 2014

(65) Prior Publication Data

US 2015/0104085 A1 Apr. 16, 2015

Related U.S. Application Data

(60) Provisional application No. 61/889,342, filed on Oct. 10, 2013.

(51) Int. Cl.
*G06K 9/00* (2006.01)
*G06T 7/00* (2006.01)
*A61B 6/00* (2006.01)

(52) U.S. Cl.
CPC .............. *G06T 7/0014* (2013.01); *A61B 6/463* (2013.01); *A61B 6/503* (2013.01); *A61B 6/504* (2013.01); *G06T 2207/10072* (2013.01); *G06T 2207/30021* (2013.01); *G06T 2207/30048* (2013.01); *G06T 2207/30101* (2013.01)

(58) Field of Classification Search
None
See application file for complete search history.

(56) References Cited

U.S. PATENT DOCUMENTS

| | | | |
|---|---|---|---|
| 623,518 | A | 4/1899 | Crook |
| 6,006,122 | A | 12/1999 | Smits |
| 6,285,903 | B1 | 9/2001 | Rosenthal et al. |
| 6,623,518 | B2 | 9/2003 | Thompson et al. |
| 6,842,644 | B2 | 1/2005 | Anderson et al. |
| 6,980,675 | B2 | 12/2005 | Evron et al. |
| 7,218,968 | B2 | 5/2007 | Condie et al. |
| 7,308,299 | B2 | 12/2007 | Burrell et al. |
| 7,321,677 | B2 | 1/2008 | Evron et al. |
| 7,327,872 | B2 | 2/2008 | Vaillant et al. |
| 7,499,743 | B2 | 3/2009 | Vass et al. |
| 7,587,074 | B2 | 9/2009 | Zarkh et al. |
| 7,697,972 | B2 | 4/2010 | Verard et al. |
| 7,742,629 | B2 | 6/2010 | Zarkh et al. |
| 7,778,685 | B2 | 8/2010 | Evron et al. |
| 7,778,686 | B2 | 8/2010 | Vass et al. |
| 7,813,785 | B2 | 10/2010 | Okerlund et al. |
| 7,996,063 | B2 | 8/2011 | Vass et al. |

(Continued)

OTHER PUBLICATIONS

Yu et al. "Cardiac Resynchronization Therapy", Wiley-Blackwell; 2 edition (May 12, 2008), pp. 205-207.*

(Continued)

*Primary Examiner* — Randolph I Chu
(74) *Attorney, Agent, or Firm* — Harness, Dickey

(57) ABSTRACT

A system including or receiving information regarding the geometry of a patient can be used to identify possible or appropriate instruments for a patient. Instruments can include pacing and defibrillation leads. Information regarding the patient can include target location size, bifurcation angles, and tortuosity of a path. Information regarding the instrument can include diameter, shape, stiffness, and/or other handling characteristics. The information can be used to identify or rank instruments.

22 Claims, 5 Drawing Sheets

(56) References Cited

U.S. PATENT DOCUMENTS

| | | |
|---|---|---|
| 8,025,622 B2 | 9/2011 | Rold et al. |
| 8,052,711 B2 | 11/2011 | Hanse et al. |
| 8,073,213 B2 | 12/2011 | Vaillant et al. |
| 8,298,147 B2 | 10/2012 | Huennekens et al. |
| 8,355,784 B2 | 1/2013 | Rochat et al. |
| 8,401,616 B2 | 3/2013 | Verard et al. |
| 8,483,829 B2 | 7/2013 | Rochat et al. |
| 8,515,527 B2 | 8/2013 | Vaillant et al. |
| 8,731,642 B2 | 5/2014 | Zarkh et al. |
| 2005/0008210 A1 | 1/2005 | Evron et al. |
| 2006/0074285 A1 | 4/2006 | Zarkh et al. |
| 2010/0298695 A1 | 11/2010 | Wenger |
| 2011/0054581 A1* | 3/2011 | Desai ............... A61N 1/05 607/116 |
| 2011/0112398 A1 | 5/2011 | Zarkh et al. |
| 2011/0144734 A1* | 6/2011 | Westlund ........... A61N 1/05 607/137 |
| 2011/0208030 A1* | 8/2011 | Stevenson .......... A61N 1/05 600/373 |
| 2011/0213260 A1 | 9/2011 | Keel et al. |
| 2012/0232478 A1 | 9/2012 | Haslinger |
| 2012/0253340 A1* | 10/2012 | Stevenson ......... H03H 7/0123 606/33 |
| 2013/0064343 A1 | 3/2013 | Verstraelen et al. |
| 2013/0116739 A1 | 5/2013 | Brada et al. |
| 2014/0330347 A1* | 11/2014 | Simms, Jr. ......... A61N 1/37217 607/60 |
| 2014/0371833 A1* | 12/2014 | Ghosh ............... A61B 19/50 607/129 |
| 2015/0206302 A1* | 7/2015 | Chen ................. G06T 7/0012 382/131 |

OTHER PUBLICATIONS

"Attain Left-Heart Leads," LV Leads for CRT Implantation with Biventricular Devices—Medtronic Brochure. (2013). 12 sheets.

"Attain® Family Left-Heart Leads and Delivery Systems," Medtronic Brochure. (2004). 6 sheets.

Attain Stability™ Model 20066. Medtronic Brochure. (2013). 4 sheets.

Biffi, Mauro et al. "Left Ventricular Lead Stabilization to Retain Cardiac Resynchronization Therapy at Long Ter: When is it Advisable," Europace Advance Acess (Sep. 26, 2013). (8 pages).

CardioGuide™ Implant System. Medtronic Brochure. (2013). 2 sheets.

* cited by examiner

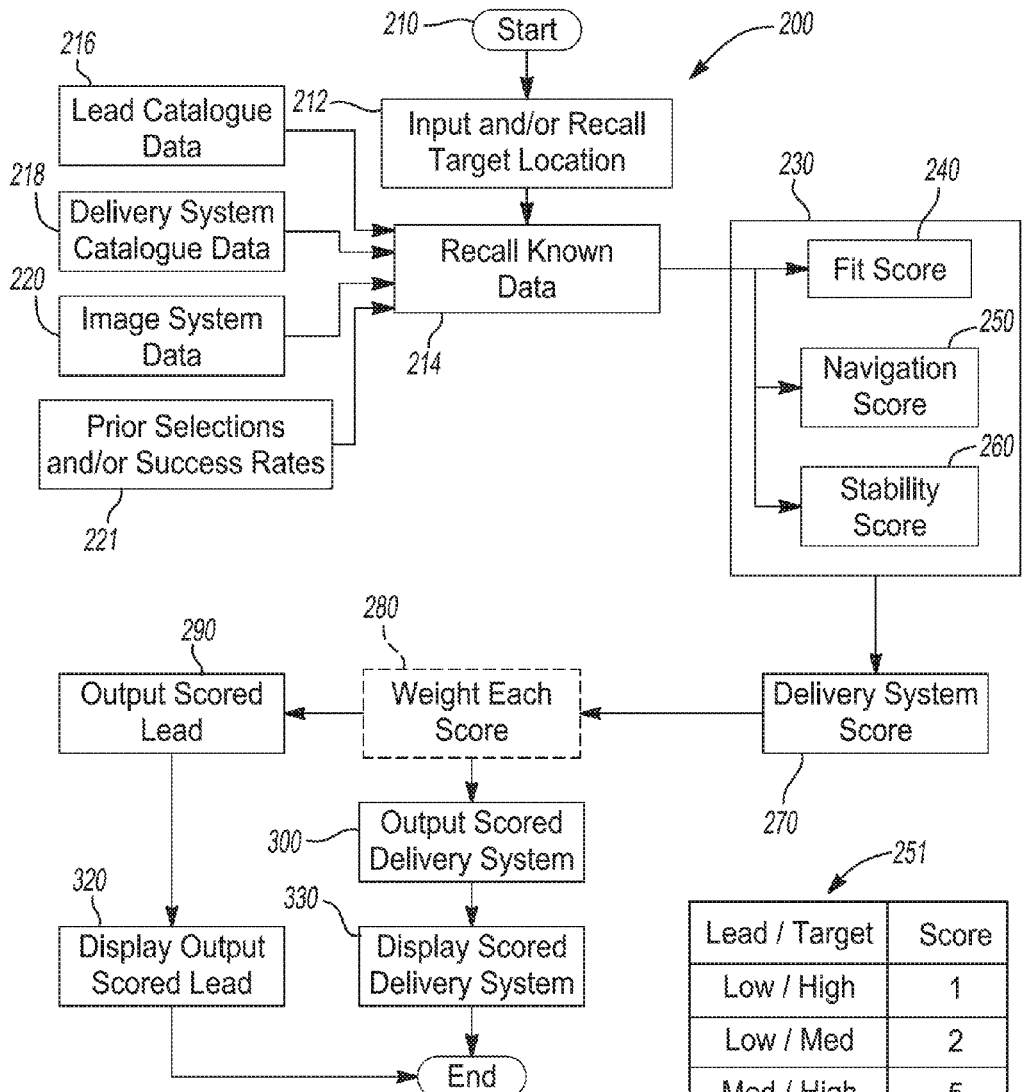

Target Location Characteristics:

| Inputs | Diameter at Target | 7 | Fr |
|---|---|---|---|
| | Tortuosity to Target | Low | ( H, M, L ) |
| | Bifurcation Angle | 30 | Degrees |

— 310
— 214

Lead Scores for Entered Target Characteristics:

| | Lead | 1 | 2 | 3 | 4 | 5 |
|---|---|---|---|---|---|---|
| 240 | Fit Score | 20 | 20 | 20 | 20 | 20 |
| 250 | Navigation Score | 10 | 10 | 10 | 10 | 5 |
| 260 | Stability Score | 3.5 | 3.5 | 1.5 | 5 | 11 |
| 320 | Total Score | 33.5 | 33.5 | 31.5 | 35 | 36 |
| 330 | Subselection Recommended? | No | No | No | No | No |

(Outputs)

— 312

METHOD AND SYSTEM FOR RANKING INSTRUMENTS

CROSS-REFERENCE TO RELATED APPLICATIONS

This application claims the benefit of U.S. Provisional Application No. 61/889,342, filed Oct. 10, 2013. The entire disclosure of the above application is incorporated herein by reference.

FIELD

The subject disclosure is related generally to a system for assisting in a surgical procedure, in particular to assisting in scoring and suggesting one or more of various instruments used during a surgical procedure.

BACKGROUND

During various surgical procedures, such as the positioning of a lead in or near a heart of a patient, a position for a lead can be selected by a surgeon, electrophysiologist, or other appropriate user. The position of the lead may be at a target location, such as in a coronary sinus of a human subject or at a branch of the coronary sinus in the heart. The positioning of the lead can include a wedging or interference fit, a passive non-interference fit, or an actively fixated position of a lead into a coronary vessel of a patient.

Various leads can include the Attain™ cardiac leads sold by Medtronic, Inc. The leads can include various shapes and configurations to be positioned into the coronary vessels or other selected locations of the patient. The leads can provide stimulation, such as with an implanted cardiac resynchronization system, including a pacemaker or defibrillator. The lead can be positioned within the patient to provide stimulation to an appropriate portion of the anatomy, such as a selected portion of the heart, to stimulate a dyssynchronous region of the heart. Generally, the lead can be positioned to stimulate a late activating portion of the heart.

A user can acquire image data of a patient, such as using known fluoroscopic techniques, including a venogram of a patient. The venogram of the patient can be used to identify selected locations for stimulation of the heart.

SUMMARY

This section provides a general summary of the disclosure, and is not a comprehensive disclosure of its full scope or all of its features.

Positioning of an appropriate lead within the patient can be based upon image data acquired of the patient and user input and experience. Generally, the positioning of a lead within the coronary vessels may need to account for the geometry of the vessels, tortuosity of a path through vessels to reach a target location, and/or diameter of the coronary vessels. The appropriate lead to be positioned within the coronary vessels, or other appropriate positions for stimulation in a patient, may be selected based upon various factors, including a diameter of the lead, other physical factors of the lead, and user experience.

Using various systems, such as the CardioGuide™ implant system sold by Medtronic, Inc., image data can be acquired of a patient to identify various portions of the anatomy. For example, image data acquired during venograms can be assimilated or reconstructed into a three-dimensional model of the coronary vasculature of a subject, such as a human patient. The three-dimensional image of the coronary vasculature can include geometric, size, and configuration information regarding various portions of the anatomy, tortuosity of a path to reach a target location, vessel size to reach a coronary vessel, size of the vessel, location of the vessel, etc. In addition to the geometric shape and configuration of the patient, image data can incorporate or include physiological data, such as contraction timing, motion change, and the like. For example, image data can be acquired at a single time to generate a static three-dimensional model. Image data may also be acquired over time, such as about 30 frames per second, to acquire contraction timing data regarding a patient.

A system receiving information regarding the geometry of a patient can be used to identify possible or appropriate leads for a patient. For example, the geometric data, such as a vessel diameter, of a patient can be used to identify a maximum or minimum in diameter of a lead to achieve a stable position relative to a selected implantation location. The take-off angle of a vessel and the tortuosity of a path can be used to identify a lead that can achieve the identified branch angle and path and achieve a stable position to a selected implantation location. Lead suggestions can include suggesting various physical parameters of a lead, such as diameters of a lead can be suggested based on a measured diameter geometry of the patient's vessel and/or coronary sinus. It is also understood that the system can be used to suggest or selected instruments in addition to leads, such as implant tools, drug delivery instruments, etc.

Further areas of applicability will become apparent from the description provided herein. The description and specific examples in this summary are intended for purposes of illustration only and are not intended to limit the scope of the present disclosure.

DRAWINGS

Example embodiments will now be described more fully with reference to the accompanying drawings.

FIG. 7 is a flowchart of a method according to various embodiments of the subject disclosure;

FIG. 8 is a table illustrating exemplary look-up data;

Corresponding reference numerals indicate corresponding parts throughout the several views of the drawings.

DETAILED DESCRIPTION

Figure 1:
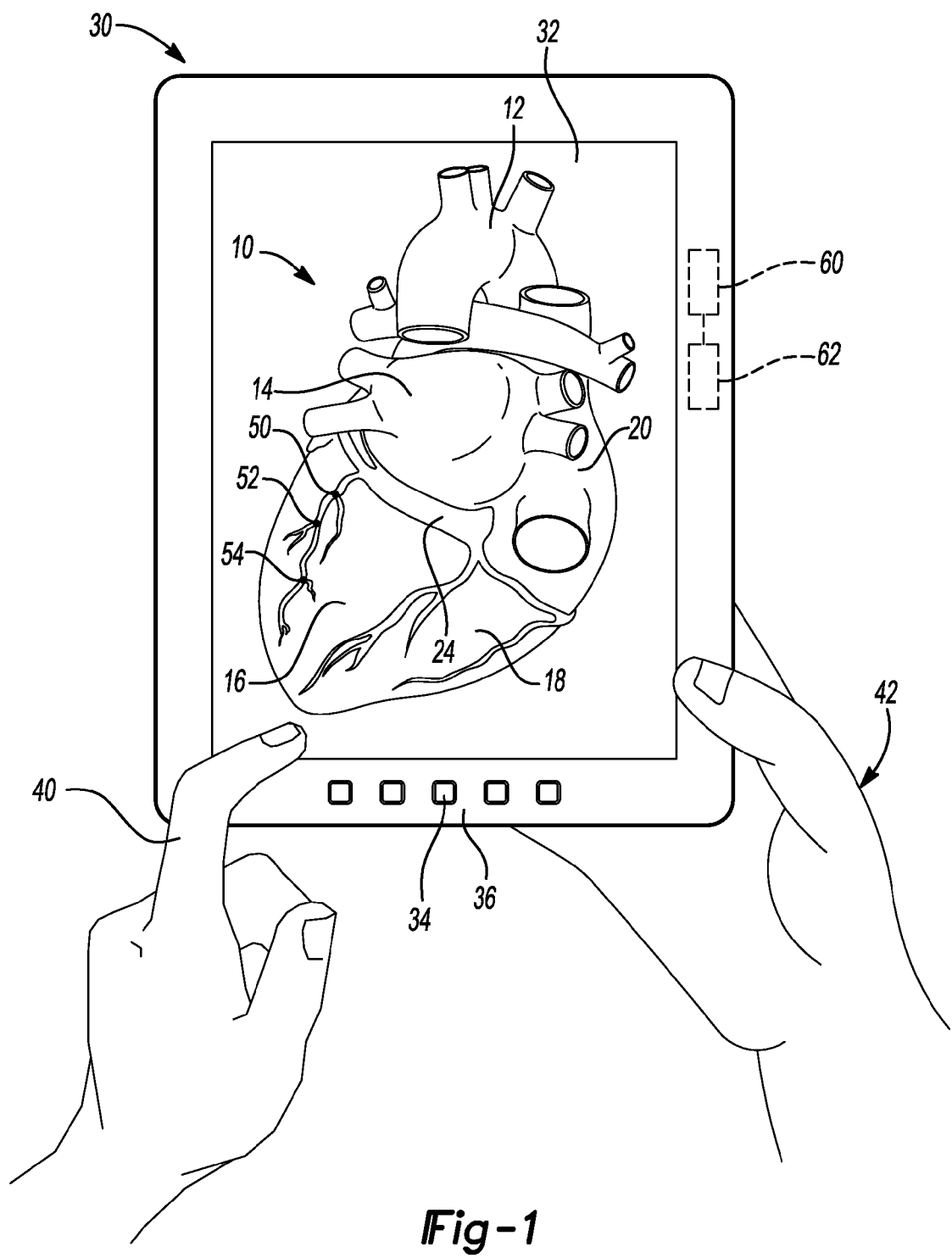
FIG. 1 is a schematic view of a display device and processor system including an input system, according to various embodiments.

Example embodiments will now be described more fully with reference to the accompanying drawings.

A system can be used to acquire image data of a patient and reconstruction a three-dimensional view of at least a portion of a subject or device. For example, image data can be acquired of a patient's heart and vessel structure and a three-dimensional reconstruction of the patient's heart and vessel structure can be made. Various systems to generate such a three-dimensional reconstruction with acquired image data include the CardioGuide™ sold by Medtronic, Inc. Additionally, various systems include those disclosed in U.S. Pat. Nos. 7,778,685; 7,742,629; 7,587,074; 7,321,677; and 6,980,675; and U.S. Pat. App. Pub. No. 2013/0116739, 2011/0112398, 2006/0074285, and 2005/0008210, all incorporated herein by reference. Generally, the patient imaging systems can acquire image data of a patient using various techniques, such as a venogram. In venogram procedures, a contrast agent is injected into a patient and x-ray images are acquired of the patient, such as a patient's coronary sinus, while the contrast agent is in and traveling through the vessels of the patient. Accordingly, one or more image of the patient is acquired with the contrast agent flowing through the patient's vessels to allow imaging of the vessels of the patient. The imaging generates image data that allows image reconstruction to be made of the patient, such as a three-dimensional (3D) reconstruction, based upon the image data that can include two or more x-ray projections. The x-ray projections may be two-dimensional projections that are used to form a reconstruction. It is also understood that a plurality of projections can be acquired of the patient over time to allow for a motion reconstruction of the patient, including motion of the coronary sinus during a heart cycle. In any case, the image data can be used to reconstruct a three-dimensional model of portions of the patient, such as the patient's heart, patient's vessel system, and the like. It is further understood that any appropriate image data can be used, such as computed tomography (CT) scan data, magnetic resonance image (MRI) data, positron emission tomography (PET) scan data, etc.

It is understood, however, that various other members can be imaged and reconstructed. For example, inanimate objects, including complex machinery, robotics, hydraulic systems, and the like can also be imaged or analyzed. For example, computer-aided design images can be used to assist in determining a geometry, size, and the like of various portions of machinery.

In various embodiments, the image data of a subject, such as a human patient or other appropriate non-human patient, can be analyzed. The analysis of the image data can be used for various reasons, such as those discussed further herein. For example, the image data can be analyzed to determine a geometry of a patient's anatomy, a size of various portions of the patient, a pathway or tortuosity of a pathway from a start point (such as an entry point) to a selected target location of the patient, and other appropriate analyses. The tortuosity of a pathway can include the number of curves or turns of the path and a size or angle of the curves. The path can be from an insertion or start point to a target location, as discussed herein.

With initial reference to FIG. 1, an image of a heart is illustrated. The image 10 may be a three-dimensional reconstruction of a heart so that the image 10 can be viewed from different angles. Further, a three-dimensional reconstruction can allow various measurements between two or more points to be made and/or compared. For example, a diameter of a vessel can be measured in the image 10.

The image 10 can include various anatomical features, including an aorta 12, a left atrium 14, a left ventricle 16, a right ventricle 18, and a right atrium 20. Various other anatomical features may include a coronary sinus (cs) 24. It is further understood that the image 10 may include other anatomical features, such as coronary vessels, musculature, etc. The image 10 may also include vessel structures leading to the heart and may be displayed on a display system 30. The display system 30 can included a display device or screen 32, input buttons or portions 34, and a case 36. The display device 30 can include a touchscreen that allows a user to touch the screen 32 to input commands, such as identifying one or more target locations.

The touch screen can allow a user to use a digit 40 to touch various locations or portions of the displayed image 10 to identify various features or target locations, as discussed further herein. The display device 30 can further be handheld or portable, such that a hand 42 of a user can be used to hold the display device 30 while the digit 40 interacts with the display device 30. The digit 40 can also be used to interact with the touch screen 32 or one or more of the buttons 34 while being held. It is understood that the display device 30 need not be handled and may be supported by a desk, table, etc. Further, the display device can be known or commercially available display devices with touch screens which may or may not include internal memory or processor systems.

Once the image 10 is acquired or reconstructed based upon the image data acquired of the selected patient, the user can identify or select a location for positioning an instrument. The instrument may be a lead that can include a lead associated or used with an appropriate implantable medical device (IMD). The IMD can be selected devices, including a cardiac resynchronization system (CRT), stimulation devices, such as those used to stimulate anatomical or physiological responses (e.g. stimulation for muscle or nervous system responses), defibrillation, and other appropriate devices. Although an example herein is directed towards the CRT and related leads positioned in or near the coronary sinus, it is understood that any appropriate lead or IMD can be used. Further, instruments can include material (e.g. drug or chemical) delivery instruments, stimulation instruments, physiological signal instruments, sensing instruments, or the like.

For positioning a lead within a heart of a patient, a lead can be used to interconnect with an implantable medical case that can include a stimulation processor, power source, catheter, and other appropriate features. It is understood that the IMD can be implanted at any appropriate location relative to the patient. The associated lead is positioned at an appropriate location, such as relative to the coronary vessels 24. Cardiac leads may include the Attain™ cardiac simulation lead sold by Medtronic, Inc. and IMDs can include the VIVA XT® IMD or the Protecta® XT CRT-D IMD also sold by Medtronic, Inc. It is understood that the specific manufacturer of the lead and IMD is not necessary for the subject disclosure. As discussed further herein, a predetermined or acquired information or characteristic regarding various features, such as shape, size, lead cant and pushability of leads and/or implantation systems (e.g. catheters) can be acquired for any particular or desired lead and implantation system.

With continued reference to FIG. 1, the image 10 can be displayed for use by the user. The user can interact with the image 10 in any appropriate manner, such as the use of the touch display 32 to identify various target locations for positioning of a cardiac lead. For example, the user can use the digit 40 to touch the screen 32 at various locations on the image 10 to identify one or more lead locations or lead target locations. The user can touch one or more target location, such as a first target location 50, a second target location 52, and a third target location 54. It is understood that the user can touch any appropriate number of target locations and that three target locations 50, 52, and 54 are merely exemplary. Moreover, the user can touch only a single target location based upon the anatomy of the patient, experience of the user, and other appropriate factors.

Once a location or multiple locations have been selected, a processor or processor system 60 can receive the selected target locations identified by the user and access a memory 62 to execute an algorithm that may be embodied in a computer program to identify or assist in selecting one or more leads, ranking leads, identifying one or more implantation systems, or ranking implantation systems, for positioning a lead at the selected target location. The memory system 62 may also have the image 10 stored thereon for being recalled and displayed on the display device 30. Further, the storage system 62 can include catalogue data for leads and delivery systems. The catalogue data can include various physical features of the leads and delivery systems for use in the algorithm and method, as discussed herein.

The processor system 60 and the memory system 62 can be any appropriate processor or memory system, including those generally known in the computer and controller art. Moreover, the processor and memory systems 60, 62 need not be incorporated into the display device 30, but one or more of the processor and memory systems 60, 62 can be separate therefrom. For example, it is understood that the display device 30 can communicate via a wired or wireless network to a separate processor and memory system that can include the algorithm instructions for assisting and identifying or ranking one or more lead or implantation systems.

Figure 2:
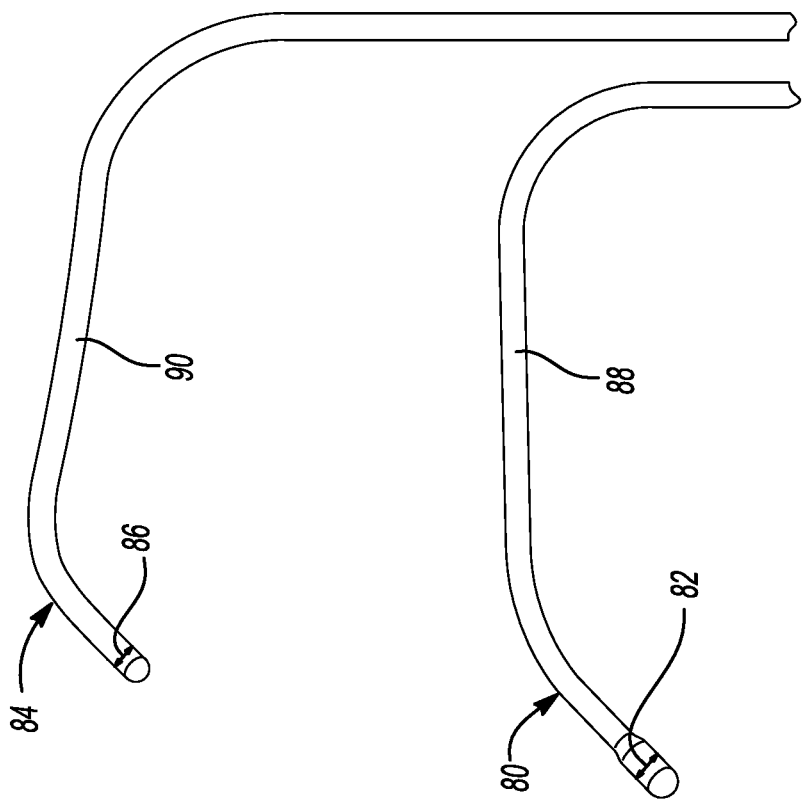
FIG. 2 is a schematic view of a plurality of exemplary leads, according to various embodiments.

With reference to FIG. 2, a first lead 80 can include various parameters and characteristics such as a first diameter 82 while a second lead 84 can include can include various parameters and characteristics such as a second diameter 86. In addition, each the leads 80, 82 can include selected and/or different handling characteristics. The handling characteristics can include various characteristics, such as the first lead 80 can include a first pushability, which can relate to a stiffness and/or modulus of elasticity of the lead 80 and the material from which it is made. Also, the first lead 80 may include a diameter along a body length 88 of the lead 80. The first lead 80 may also include other selected handling characteristics, such as a specific or selected torquability, steerability, or other characteristics that may be based on or related to a geometry or other feature of the first lead 80. The second lead 84 may include various handling characteristics that may be different from the handling characteristics of the first lead 80, for example, the second lead 82 may include a second pushability, steerability, torquability, and/or diameter of the body 90. The diameters can include or be cross-sectional diameters of the leads.

Figure 3:
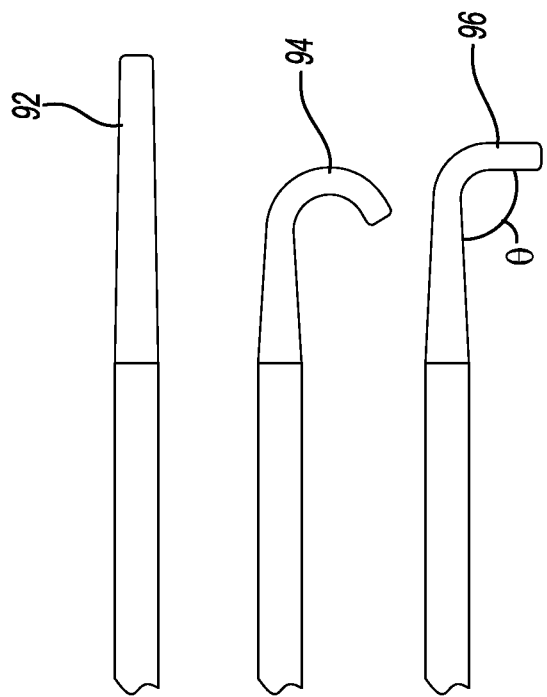
FIG. 3 is a schematic view of a plurality of exemplary catheters, according to various embodiments.

With reference to FIG. 3, lead systems can include one or more distal tip geometries, including a straight distal tip geometry 92, a curved distal tip geometry 94, or an angled distal tip geometry 96. Each of the distal tip geometries 92-96, as exemplary illustrated in FIG. 3, can be used depending upon a geometry of the target location for positioning a lead within the patient. Also, the angled tip 96 can have a cant angle 8 and may vary depending upon the selected lead tip.

It is understood that each of the lead geometries, catheter geometries, lead sizes, and the like can include a plurality of additional leads and catheter sizes and geometries. Each of the possible leads and delivery systems may have information that is known and provided by lead or catheter producers, measurements by a user or user team, or other provided information. The information can be identified as a part of a data stored with the storage system 62. The data can be referred to as a look-up table, catalogue data, or the like for access by the algorithm stored in the storage system 62 and accessed or executed by the processor 60.

Figure 4:
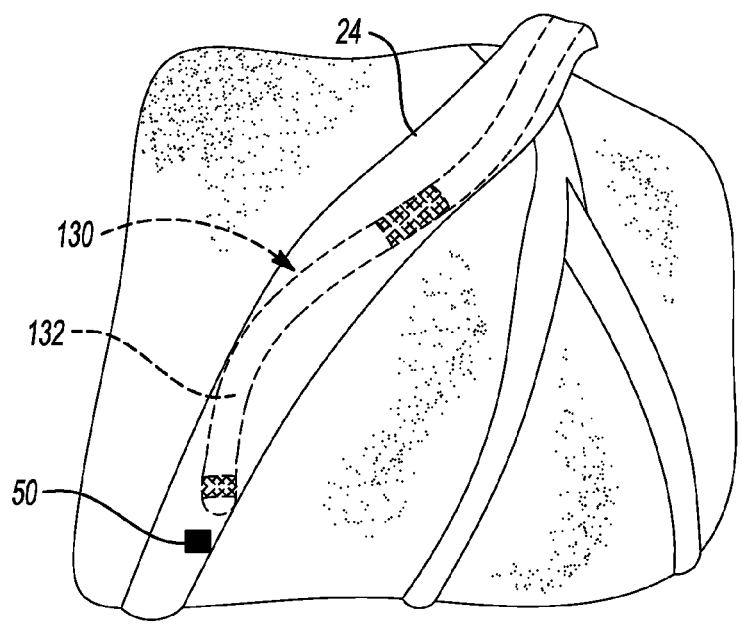
FIG. 4 is a detail view of an exemplarily implanted cardiac pacing lead.

With reference to FIG. 4, it is generally understood in the art, the lead or a selected implantation lead 130 can be selected or identified to be positioned within a selected portion of the anatomy, such as the coronary vessels 24, in a selected target location, such as the target location 50. The lead 130 can include a geometry, such as a cant or proximal bend 132 to assist in contacting portions of the anatomy to ensure that the lead 130 maintains a desired position at the target location within the anatomy. Accordingly, leads of various geometries and configurations can be provided for use in specific patients and can be selected based upon anatomical features and restrictions of a specific patient. It is understood that the various selectable leads may have appropriate geometries, such as straight, and/or various active fixation systems, such as active fixation systems (e.g. helixes, clamps, etc.). The system disclosed herein may be operated to assist in suggesting any selected lead based on the various factors, as discussed herein. Generally, the system can make the suggestion by a processor executing instructions of a program (e.g. a computer program) based on an algorithm for selecting a lead as disclosed herein. The currently disclosed system can assist in identifying and/or suggesting leads that may assist in ensuring appropriate movement, including navigation, to the target location of the lead and appropriate fixation at the target location of the lead along with or in conjunction with implantation systems that can assist in placing the lead at the desired target.

Figure 5:
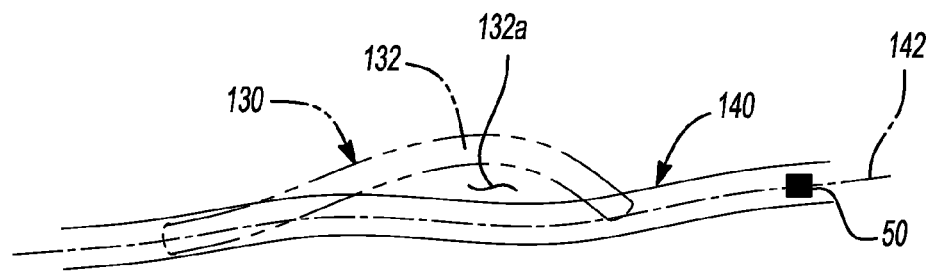
FIG. 5 is schematic view of an possible implanted cardiac pacing lead, according to various embodiments.
Figure 6:
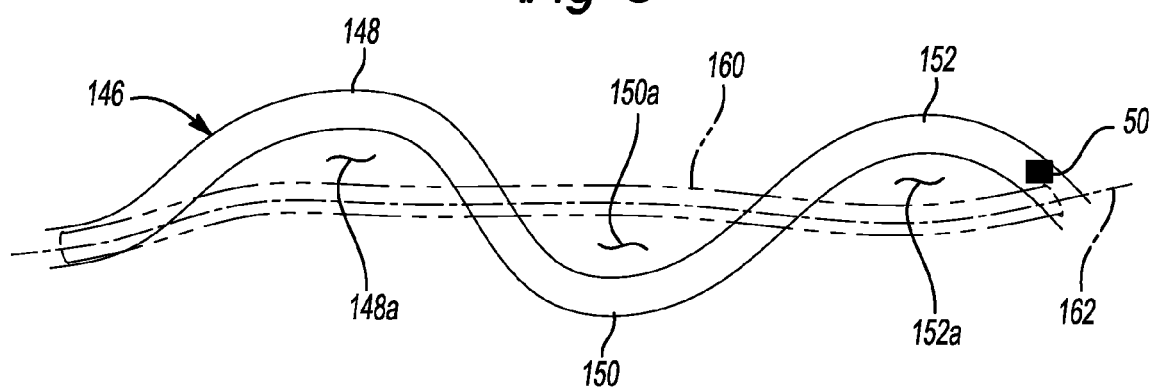
FIG. 6 is a schematic view of an exemplarily implanted cardiac pacing lead, according to various embodiments.

With reference to FIGS. 5 and 6, various leads can be positioned relative to selected vessels of the anatomy. For example, as illustrated in FIG. 5, a selected vessel 140 is illustrated. The vessel 140 may be a model of vessel based on a reconstruction, such as a three-dimensional (3D) reconstruction of the patient's vessel based on image data of the patient. The vessel 140 may include a longitudinal axis 142 and the vessel 140 is generally straight along the longitudinal axis 142, at least near at least one of the selected targets 50. In an alternative example, a vessel 146 may have one or more curved portions, including a first curved portion 148, a second curved portion 150, and a third curved portion 152. The target location 50 may be near the third curved portion 152.

As illustrated in FIG. 5, the lead 130 is illustrated relative to the vessel 140. The lead 130 includes the curved or canted portion 132. Thus, in the schematic view illustrated in FIG. 5, the lead 130 (shown in phantom) extends out of the vessel 140, at least at the curved region 132. An interference region 132*a* may be defined as an area or volume that is between the lead 130 and the vessel 140. The size or magnitude of the interference region 132*a* can be used, as discussed herein, to assist in suggesting the appropriateness of the lead 130 for placement in the vessel 140 near the target 50. It is understood that other leads can also be modeled or schematically placed near the vessel 140 to determine an interference region for the different lead.

With reference to FIG. 6, a lead 160 is illustrated schematically (in phantom) relative to the vessel 146. The lead 160 may generally extend along a longitudinal axis 162 that is substantially straight, at least relative to the vessel 146. Interference regions, therefore, can be formed between the lead 160 and the curved portions of the vessel 146. For example, a first interference region 148*a* may be defined as an area or volume between the lead 160 and the vessel 146 at the first curved portion 148. Similarly, a second interference region 150*a* and a third interferer region 152*a* may be defined between the lead 160 and the second curved region 150 and the third curved region 152. The total volume of the various interference regions 148*a*, 150*a*, and 152*a* can be used to determine a suggested lead, as discusses further herein. The lead 160, having a general shape that is straight, is different than the shape of the vessel 146. Thus, an interference between the lead 160 and the vessel 146 will exist which can assist in maintain the lead 160 in place within the vessel 146.

With reference to FIG. 7, a flow chart 200 illustrates an exemplary method for scoring and/or suggesting instruments. The method can be implemented as an executable program that uses an algorithm for scoring the instruments. The instruments can include leads that are being identified as possible leads and/or delivery systems for positioning a lead at a selected location or target location within a patient. Thus, it is understood, the method 200 can be automatically executed by the processor system with the inputs discussed herein. It is further understood, various portions of the method may include manual input, such as inputting a target location.

With continued reference to FIG. 7 in flowchart 200, an algorithm or process for scoring or identifying suggested leads begins at Start block 210. A target location may then be input and/or recalled in block 212. As discussed above, a user can input a target location with the display device 30, or other appropriate input device. For example, a user can use a cursor, a mouse cursor, or other appropriate systems to input a target location. The target location can be identified relative to an image, such as a two dimensional image or a reconstructed three-dimensional image, or an identified location using other location identification mechanisms. For example, the user can simply input an identified location, such as the target locations 50, 52, 54. The various or single selected target location can also be determined substantially automatically, based on various target selection criteria. Thus, a user input to select target locations is not required. Moreover, one or more target location can be recalled in block 212 that has been previously saved or identified.

Nevertheless, a target location can be input or recalled in block 212. Known data can then be recalled in block 214. Known data recalled in block 214 can be any appropriate data that has been previously identified or determined. The known data can be based on mechanical measurements, computer-aided drafting measurements, or appropriate information. The known data can include the physical characteristics, such as diameter and pushability or other handling characteristics, of possible leads and delivery systems. Moreover, imaging data of a subject, such as imaging data of a heart of a patient, can be analyzed to determine various features, including measurements and geometry thereof, and this can also be known data that is recalled.

Various data recalled in block 214 can include lead catalogue data in block 216. Lead catalogue data from block 216 can include information such as a diameter of a lead, a diameter of a tip or other body portion of a lead, a flexibility or pushability (or other handling characteristics) of a lead, a geometry of a lead, a cant of the lead, bend of the lead, or other appropriate information. For example, the geometry of the Attain™ cardiac leads can be recalled or accessed by the method 200. The lead catalogue data from block 216 can include information regarding any appropriate lead or leads, including those sold by Medtronic, Inc., those sold by other cardiac lead producers, or a patient-specific lead. The lead catalogue data can be provided by the producers or generated by measurements made by the user or other measuring body.

Other information recalled into the block 214 can include a delivery system catalogue data in block 218. Delivery system catalogue data can include data regarding the geometry of various lead delivery systems, including catheters, guide wires, or subsystems provided by various producers. For example, the catheter subsystem can include the ATTAIN-SELECT® II sub-selection catheter, sold by Medtronic, Inc. and can include many other catheters. Each of the catheters may have a geometry and a stiffness that differs from other catheters. For example, a catheter may include a distal curve, two or more distal curves, or a straight geometry. Moreover, the delivery systems can include a stiffness and geometry to assist in positioning a lead in a desired location or target location. Accordingly, the information regarding the stiffness, pushability, geometry, distal geometry, diameter, and other appropriate information can be recalled in the block 214 from the delivery lead system catalogue data in block 218.

Additionally, image system data in block 220 can be recalled known data into block 214. Image system data from block 220 can be any appropriate image data, including that discussed above. For example, the CardioGuide™ cardiac imaging system can acquire and reconstruct three-dimensional image data regarding a selected anatomy. As discussed above, the reconstructed heart image 10 can be based upon image data that is acquired with a selected imaging system. The reconstruction of the heart image 10 can be used to identify various features, such as geometries, sizes, motion, and other appropriate information regarding a subject.

Accordingly, the image system data in block 220 can include geometry, size of a target, diameter of a vessel, geometry of a vessel, geometry of a coronary sinus, tortuosity of a path from a start point to a target location, motion of a subject or specific portion of a subject, and other appropriate image data. Motion data of a subject can include activation timing of a heart of a patient, portions of the subject moving over time, physiological timing data, and other appropriate motion data. Image data can also include the tortuosity of a path from an entry point to a target location, a diameter of a target location, a diameter of a vessel from the entry point to the target location, a diameter of a vessel from the target location to a distal end of the vessel, and other appropriate image data.

The recalled known data in block 214 can be used as a part of the method 200 to assist in identifying selected or possible leads and/or delivery systems for positioning a lead in a selected location. As discussed above, the example discussed and illustrated specifically here includes a cardiac system, including a target location in the coronary sinus and/or at a left ventricle to stimulate a portion of a heart. It is understood, however, that leads can be positioned at any appropriate portion of the anatomy to stimulate or provide treatment to a portion of the anatomy. Moreover, it is understood that a lead need not stimulate a portion of the anatomy with an electrical stimulation, but can provide a treatment, such as the delivery of a pharmaceutical compound.

The recalled known data, including image data, lead catheter data, delivery system catalogue data, and other appropriate data can be recalled in block 214. The recalled data from block 214 can be combined with the input and/or recalled target location from block 212 to determine various scores in score block 230. Score block 230 can include one or more scores or scoring algorithms that can be used to score various portions of an implantation procedure. For example, a fit score 240 can be determined based upon the input data. Moreover, a navigation score 250 can be determined regarding the input data. Also, a stability score 260 can be determined based upon the input data. The various scores in the score block 230 can be used to assist in identifying or suggesting selected leads and/or delivery systems, as discussed further herein. The scores from score block 230 can be used to analyze the target location input in block 212 and recalled known data in block 214 to assist in identifying selected and/or appropriate leads and/or delivery systems for the target location based upon the recalled data, including lead catalogue data from block 216, delivery system catalogue data in block 218, and image system data recalled from block 220.

Initially, the fit score in block 240 can be a score or number that is based upon a relative measurement of a diameter of a lead as compared to a diameter of a target. As discussed above, the diameter of the target can be identified or determined based upon the image data from the image data system in block 220. The diameter of the lead can be recalled from the lead catalogue and data in block 216. A comparison or relative measure, such as a ratio, between the two can be used to determine a fit score. For example, a 1 millimeter diameter lead can have a fit score of 1.0 for 1 millimeter diameter target. It is understood, however, that a target that is within a soft tissue, can have a slightly flexible diameter. Accordingly, a diameter of a vessel in the heart can be about 1 millimeter, but can be understood or known to have a flexible diameter of a selected percentage, such as about 5%, 10%, or any appropriate amount. Accordingly, a target diameter of about 1 millimeter can have a determined target diameter within a range, such as about 0.8 millimeter to about 1.2 millimeters. Given that a portion of the anatomy may flex, a lead having a slightly larger diameter than the diameter of the target and may still be given a score that would allow it to be identified as a possible appropriate lead although the lead diameter is greater than the target location diameter.

In one example, a score of 1.0 can be determined for a diameter of the lead that matches the diameter of the target (e.g. 1 millimeter lead and a 1 millimeter target). A lead that is larger than the target, such as a 3 millimeter lead, can have a score that is less than 1.0. Any appropriate value can be given to the score, including a weighted value as discussed further herein, to achieve a selected result, such as ease of access to the target location. If a greater value score is given to a better or more optimum fit, then the scores may be summed to provide a lead score, which can be an overall score for the selected lead. It is understood that weighting can be applied to each score as well prior to the summation.

Generally, the fit score can be a value or a score that relates to a possible fit of the lead relative to a target. That is, that the lead would fit into the target and can be navigated along a vessel path to the target. As discussed above, and in further detail herein, a stability score and a navigation score can also be determined. Accordingly, the fit score may only be related to a relative size of the lead to the target location. A stability score and/or navigation score can be based upon the ability to move the lead to the target location and the ability or likelihood that the lead would be maintained and stable in the location of the target. Accordingly, the fit score can be limited to a fit or ability to fit a lead into a selected target.

The navigation score in block 250 can include a score that is a relative measure of how complex a path is from an entry point or other selected starting point to the target location compared to an estimate of the ability of a lead to reach the target based on the complexity of the path. The complexity of the path can be identified as a tortuosity amount, including a low tortuosity, a medium tortuosity, or a high tortuosity or other measure of path complexity. A tortuosity can include a measurement or an estimation of a number of curvature and/or twist, a radius of the curvatures and/or twists, and a length of the curvatures and/or twists, and other appropriate measurements between a starting point and a target location. Accordingly, the image data acquired from block 220 can be used to identify the tortuosity of the path from the entry location to the selected target. A tortuosity can be identified based upon the image data in the selected target location and the start point.

A lead, such as a lead from the lead catalogue in block 216 either alone in combination with a delivery system from block 218, can have a related ability to navigate or move through a given tortuosity. Each of the leads can be predefined regarding the handling characteristics thereof. For example, an ability to move through a tortuosity based upon various characteristics of the lead and/or delivery systems, including stiffness, pushability, diameter, shape, and the like. Accordingly, each lead and/or delivery system can have a predefined ability to move through a selected tortuosity of a path. Accordingly, a look-up table can be created based upon each lead and/or delivery system relative to its ability to move through a tortuous path.

With reference to FIG. 8, a look-up table 251 can be stored and saved to be recalled in block 214 to determine a navigation score based upon the identified tortuosity in the selected target and take-off angle of the target vessel. For example, as illustrated in FIG. 8, a lead that has a "low" ability to pass through a tortuous path will have a score of 1 if the path is identified as "high" tortuosity. However, a lead having a "high" or great ability to go through a tortuous path and "low" tortuous path can have a score of 10. The score can be incorporated with the other scores, as discussed further herein, to provide a lead score to identify or assist in identifying a selected lead and/or delivery system.

Finally, in block 216 a stability score can be determined. The stability score can be based upon various factors, such as a bifurcation of the target vessel, a tortuosity of the path, a lead shape, and a tightness of fit. Each of the factors are parts of the score, either alone or in combination, can be used to determine the stability score to assist in identifying an appropriate lead.

Figures 9, 10:
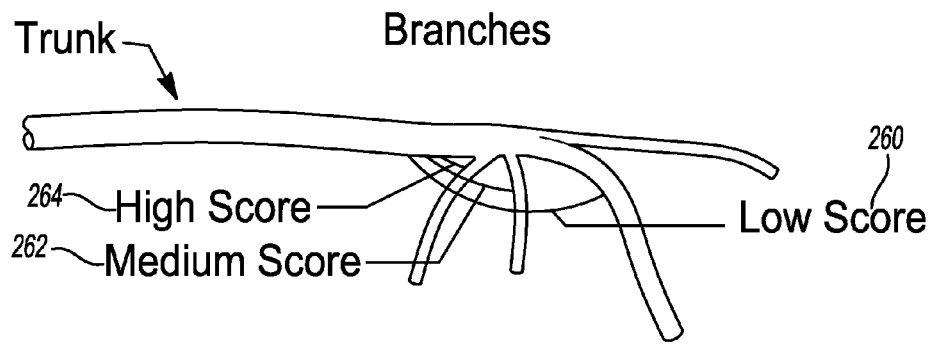
FIG. 9 illustrates exemplary branching angles.
FIG. 10 illustrates an exemplary output display.

A portion of the stability score can include a bifurcation angle or take-off angle of the target vessel. The target can be identified by a user, as discussed above, at a selected location. For example, the target can include a location of the coronary sinus that has a trunk that bifurcates into one or more a branch vessels. With reference to FIG. 8, a large (e.g. obtuse) angle bifurcation 260 can be given a low score, indicating a relatively lower likelihood that the lead will remain stable at that location. A medium score can be given to a bifurcation branch vessel that has a less obtuse angle 262, such as an angle that is about 90° relative to the trunk vessel. A high score can be given to a bifurcation branch vessel that has a low (e.g. acute) angle 264 relative to the trunk vessel, indicating a relatively higher likelihood that the lead will remain stable at that location. As illustrated in FIG. 9, a relative low, high, or medium score can be identified for selected bifurcation angles of the different branch vessels depending upon a branch angle from the trunk vessel. It is understood that each of the branch angles can be a discrete value and a discrete value can be given for scoring. However, it is also understood that a range and a relative score can also be identified for each of the bifurcation angles.

A tortuosity can also be a part of the stability score. As discussed above, tortuosity can be identified in various amounts, such as high, medium, or low. Further, a high tortuosity path and/or location of the target can increase an ability of a lead to maintain its location. The stability score can be a score of the ability of a lead to maintain its implanted location at the target location of the patient. Accordingly, a highly tortuous path can assist in resisting movement of the lead once it's located at the target location. A low tortuous path, however, can allow for easier movement to the lead from a selected location and can, therefore, be given a lower stability score.

A lead shape can also be used to assist in determining the stability score. For example, leads can be any appropriate shape, including shapes of leads included with the Attain™ cardiac leads provided by Medtronic, Inc. Leads can include various shapes or configurations, such as a canted shape or a straight shape, or S-shaped. In a canted lead, a distal tip portion can be angled relative to the proximal portion. The canted shape or configuration of the lead can assist in maintaining the lead in the target location. Accordingly, a canted lead can have a higher stability score than a straight lead.

A tightness of fit can also be a part of the stability score. In particular, a tighter fit of a lead relative to a target location can mean that the lead is more stable over time. For example, if a target location is 1 millimeter in diameter and a lead is 1 millimeter in diameter a score of 1.0 can be determined, or any appropriate number. However, if a target location is 1.0 millimeters in diameter and a lead is 1.2 millimeters in diameter a tightness score can be higher, such as 1.2. Accordingly, a lead that is larger than the target location will be tighter in the target location than a lead that is equal to or smaller than the target location. Although, as discussed above, a fit score can be determined based upon whether or not a lead can reach the target location, a tightness score can be based upon whether the lead will be stable or maintained in the target location after implantation. Also, as discussed above and generally understood by one skilled in the art, soft tissue can be relatively elastic. Accordingly, a lead that is slightly larger, such as about 1% to about 20% larger, including about 3% to about 10% larger, than the target location's diameter can cause the soft tissue to expand around the lead and hold it tightly in place.

Further, it will be understood that the stability score can include a combination of the various parts discussed above. For example, a lead shape and tightness of fit can be combined or averaged into a metric that accounts for both the lead shape and the tightness of fit. For example, a difference analysis or area under the curve analysis between the shape of the lead and the shape of the target vessel can be used to determine the ability of the lead to reach and be maintained in a target location. Accordingly, a stability metric can also be included or added to the stability score either in addition to the portions discussed above or to replace the various portions, including lead shape and tightness as individual factors, for determining the stability score.

Returning reference to FIGS. 5 and 6, the area in the various inference regions, whether one or more than one, can be the area under the curve, such as the area between the analyzed lead and a wall of the vessel. The total area can be used to determine a general stability of the selected or analyzed lead within a vessel near the target 50, or any selected target. It is understood, however, that too great an area under the curve may not allow the lead to reach the selected target. Thus, a metric can be chosen to determine an appropriate range for the area, such as the total interference region, to assist in suggesting a lead for implantation. Further, the metric can include weighting for positions of the interference regions. For example, a distal interference region may be weighted greater than a proximal interference region.

A delivery system score in block 270 can also be determined. The delivery system score can be determined based upon the same factors as those discussed above, such as the determined tortuosity of a path, a target location, a bifurcation or take-off angle, and other factors. A delivery system can include a guide wire, catheter, or other system that assists in delivering a lead to the target location. In one example, a "subselection" catheter can include an angle, such as a 130° distal tip angle, to assist in sub-selecting the target vessel take-off and locating a lead at a selected target location. The subselection catheter can be scored based upon the ability of a lead to reach a target location and/or a possible necessity of a delivery system to position a lead at a target location. For example a very sharp take-off angle of the target vessel may prevent the lead to access the target vessel. The subselection catheter can help to access the vessel and provide enough support to create the pushability for the lead needed to overcome this tortuous part of the target vessel. It will be understood that a delivery system score in block 270 can range between a score that would determine that a delivery system is not suggested to be used or necessary to a score that would suggest that a delivery system be used.

A weighting system may be applied in block 280. Weighting the scores is not required, but can be used to assist an algorithm in determining or identifying possible leads. The weighting in block 280 can individually score or weight each of the scores determined for the various leads, such as the fit score from block 240, the navigation score from block 250, the stability score from block 260, and/or the delivery system score from block 270. The weighting system can be a simple weighting system, such as a multiplication or order given to each of the scores or any other appropriate weighting system. Alternatively, it can be determined that no weights are provided to any of the scores and that they are simply summed to assist in identifying a selected lead.

The scores can be summed or otherwise calculated into a lead score that is based on all of the scores determined in the method 200. It is also understood, that a final lead score that is used to suggest an optimal lead and/or delivery system can be based on less than all of the determined scores. Nevertheless, in various embodiments, the lead score can be based on a weighted or unweighted summation of the scores to suggest an optimum lead and/or delivery system. The optimum lead and/or delivery system can be one that is suggested to optimally attain a selected result of a procedure.

After the scores are determined in the score block 230 and the delivery system score in block 270, and with any possible weighting if desired or determined, outputs of the scores can be made. The lead score can be output in block 290 and the delivery system score can be output in block 300. According to various embodiments, the outputs can include a single output, multiple outputs, a table of outputs, or other appropriate outputs. The outputs can also be displayed in displayed scored lead output in block 320 and display scored delivery system output in block 330. In one example, illustrated in FIG. 10, a table can be provided that includes the inputs to the algorithm or the method in block 200 in an input table portion 310 and a ranking of lead outputs in table 312.

The outputs can be numerical value outputs and/or positive or negative outputs. For example, for specific lead and/or delivery system the output can be a discrete numerical output for the selected lead. In the alternative, or in addition thereto, the output may be a "yes" or "no" as a suggestion. The outputs can be displayed, as discussed below and illustrated in FIG. 9.

The ranking or scoring of the lead outputs in table 312 can rank or provide individual scores for a plurality of leads that can be identified as various features, including model numbers, such as 1, 2, 3, 4, and 5. Further, the subselection or delivery system recommendation and/or score from block 300 can be included as a part of the output table 312, such as whether a sub-selection or delivery system is recommended or not. Moreover, it can be further included that at selected delivery system or sub-selection can be identified in the output table 312.

The outputs can be output in any appropriate manner, such as an output to a supplier to supply an appropriate lead to a user, an output to a printer system to print an invoice or pull order to deliver a lead to a user, or an output to a display device, such as the display device 30. Accordingly, in block 320, the output score lead can be displayed and in block 330 the display score for the delivery system can be displayed. Again, the displays can display numerical scores for each of the determined scores, the overall lead score, and/or the delivery system score. Moreover, a non-numerical "yes" or "no" and/or "good", "better", and "best" display may be provided. The user can view the outputs to assist in determining the appropriate lead for a selected procedure and continuing the procedure. Also, the output may include a list or ranking of leads that are suggested to not be used for a selected procedure. Thus, a user may select a lead that from all possible leads that area not negatively ranked or suggested.

The method 200 can then end in block 314. Accordingly, the user can view the outputs in blocks 320 and 330 to assist in identifying or selecting a lead and/or delivery system. The outputs can be based upon the scores discussed above, including predetermined or known information regarding the features of the leads and/or delivery systems, including handling characteristics, diameter, and other features. Accordingly, the output scores and/or recommendations can provide recommendations based upon physical characteristics of the leads and/or delivery systems. The output, however, can also be based upon the information provided of the selected subject of patient, such as with the image data recalled from block 220, which can be acquired with various selected systems.

It is understood that the scoring and output of method 200 can be done at any appropriate time. For example, the method 200 can be performed prior to preparing a patient for a lead placement procedure and the suggested lead can be prepared and delivered to a user. Alternatively, the method 200 can be used to suggest a lead from a plurality of leads available after a patient is prepared for a procedure, such as within an operating room setting.

According to various embodiments, a subject, such as a human patient can be prepared for a procedure. For example, a procedure using the CardioGuide® system may involve coronary sinus cannulation, occlusive venograms, and/or construction of a 3D model of the coronary vessels of the patient. The method 200 may be used after the user has selected a candidate left ventricular pacing target location, such as using the 3D model. If selection of implantation of other leads is selected, this may occur before or after implantation of a right atrial and/or right ventricular leads. If appropriate imaging data is available prior to a procedure, the method 200 could also be used to suggest leads at that time to ensure a correct product, such as selected specific lead, is available and present in the procedure room. For example, imaging can occurring during a separate procedure, including a coronary angiography, assuming that the separate procedure took place close enough in time so that the image data can be clinically relevant for the scheduled lead implant procedure.

Accordingly, as disclosed herein, a system can be used to make various suggestions based upon an analysis of provided information. For example, lead suggestions can include suggesting various physical parameters of a lead, such as diameters of a lead can be suggested based on a measured diameter geometry of the patient's vessel and/or coronary sinus. It is also understood that the system can be used to suggest or selected instruments in addition to leads, such as implant tools, drug delivery instruments, etc.

In addition, or alternatively to, providing a suggestion based on physical parameters of various leads and the analysis of the selected vasculature, analysis of previous procedures may also be used. For example, with reference to FIG. 7, an additional input into the Recall Known Data block 214 may be Prior Selections and/or Success Rates (herein "prior selections") block 221. The prior selections block 221 can include information regarding prior or previous procedures. For example, which leads were selected based upon anatomical analysis and scores, as discussed above, and/or the success rates of those selections. Success rates can be known based on follow-up procedures and analysis of patients after implanting a selected lead. Recalled known data in block 214 can include information regarding prior procedures that are performed on patients or subjects other than the current subject for which the image system data in block 220 is selected and the various scores in block 230 are determined. Accordingly, the prior selections block 221 can include information regarding procedures that occurred prior to and in patients other than the current patient.

For example, prior selections block 221 can include information that is collected and stored in selected databases, such as stored in appropriate memory systems, based upon an analysis and scores determined for an anatomy of prior patients or subjects and the leads selected to be positioned in those subjects. For example, the prior selections block 221 can include an analysis of a patient to determine a fit score, a navigation score, and a stability score based upon an analysis of the anatomy of the prior patient. A prior lead that was selected for the prior patient based upon the prior score can also be saved as associated with the scores for the prior patient. This information can then be used in a present procedure to assist in augmenting a suggestion made in the present procedure or in providing an additional lead suggestion. As the prior selections are associated with delivery scores (such as those generated in blocks 230 and 270), the prior selections block 221 can be used to relate to a current patient scored in block 230 that provides a delivery system score 270. A search of the database can be used to determine whether a prior patient included a similar or identical score and determine the lead used with the prior patient. A display of the lead selected for that the prior patient with the same score can be made. Additionally, interpolation can be made between scores if there is no patient with an identical score. Further, the rate of success of a selected lead based upon a delivery system score in block 270 can also be displayed. For example, based upon a selected delivery system score in block 270, a lead may have a certain percentage of cases in which it was implanted in prior patients, such as 95 percent.

Additionally, prior selection block 221 can also have success rates associated with leads that were implanted in prior patients. During follow-up procedures a success rate of, for example, a lead maintaining its selected implanted location, achieving selected results at the selected implant location, and other characteristics can be associated with the previously selected leads and anatomy scores related to those leads. This information can also be displayed relative to the previously selected leads of prior patients.

Accordingly, it is understood, that prior selections and/or success rates in block 221 can be used to assist in providing a suggestion for a current lead for a current patient. Thus, a current analysis of image system data from block 220 of a current patient that is used to determine a score in block 230 can be compared to previous procedures that are input from the prior selections and/or success rates block 221 to provide a suggestion based upon prior procedures. In various embodiments, therefore, at least one suggested lead made to a user (e.g., a surgeon) can be based upon previously selected leads that relate to or are associated with a selected anatomical analysis and/or score of a prior patient.

According to various embodiments, with prior selections and/or success rates block 221, any score from block 230 (including the fit score 240, navigation score 250, and stability score 260) may be bypassed entirely. The system, including and/or executing the method 200 discussed above, in this case may display to the user, such as the surgeon an analysis based directly on the prior selections and/or success rates block 221. For example, the display may include "Based on the physical measurements of the target location, 95% of surgeons would select lead: "Model XYZ"." Thus, a direct scoring from block 230 based on possible leads may not be made or necessary, but rather only a recall and display of prior selections may be made and displayed.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail. Moreover, specific exemplary embodiments are discussed with different features and this does not mean that they cannot be combined and/or eliminated in embodiments, unless specifically disclosed otherwise.

What is claimed is:

1. A method to assist in identifying at least one of a lead or a delivery system of the lead to a target location, comprising:
   determining with a processor system at least one score of a fit score, a navigation score, and a stability score, for the lead to be moved to and implanted at the target location;
   recalling with the processor system image data analysis to assist in determining the at least one score; and
   outputting at least one lead and the determined at least one score for the at least one lead including displaying an identification of the at least one lead;
   wherein the recalled image data analysis is based on image data acquired of a subject at the target location;
   wherein the at least one lead can be implanted at the target location.

2. The method of claim 1, further comprising:
   recalling with the processor system a lead catalogue of the at least one lead and related lead physical data;
   wherein the determined at least one score includes executing with the processor system a program to compare the related physical data of the at least one lead with at least one of the target location and a path to the target location.

3. The method of claim 2, wherein the recalled image data includes at least a three-dimensional reconstruction of the target location and at least one geometrical measurement of the target location.

4. A method to assist in identifying at least one of a lead or a delivery system of the lead to a target location, comprising:
   recalling with a processor system a lead catalogue of the at least one lead and related lead physical data;
   recalling with the processor system image data analysis to assist in determining the at least one score;
   determining at least one score of a fit score, a navigation score, and a stability score, for the lead to be moved to and implanted at the target location; and
   outputting at least one lead and the determined at least one score for the at least one lead;
   wherein the at least one lead can be implanted at the target location;
   wherein the determined at least one score includes executing with the processor system a program to compare the related physical data of the at least one lead with at least one of the target location and a path to the target location;
   wherein the recalled image data analysis is based on image data acquired of a subject at the target location;
      wherein the recalled image data includes at least a three-dimensional reconstruction of the target location and at least one geometrical measurement of the target location;
   wherein the fit score is related to a ratio of a diameter of the at least one lead recalled from the lead catalogue and the at least one geometrical measurement of the target location.

5. The method of claim 3, wherein the navigation score is related to a ratio between a determined tortuosity of the path to the target location and a determined ability of the lead to move along the determined tortuosity of the path.

6. The method of claim 3, wherein the stability score is a relative measurement of an ability of the lead to remain stable at the target location based on at least one of a bifurcation angle of a vessel at the target location, a determined tortuosity of the path to the target location, a lead shape, and a tightness of a fit of the lead at the target location.

7. The method of claim 3, wherein the at least one lead includes a plurality of leads;
   wherein the lead catalogue includes lead physical data for each lead of the plurality of leads;
   wherein the at least one score includes a lead score for each lead of the plurality of leads that is based on all of the fit score, the navigation score, and the stability score.

8. The method of claim 7, further comprising:
   displaying the lead score for each lead of the plurality of leads.

9. The method of claim 8, further comprising:
   weighting each of the fit score, the navigation score, and the stability score;
   wherein the lead score is based on the weighting of each of the fit score, the navigation score, and the stability score.

10. The method of claim 8, further comprising:
    determining a delivery system score for each lead of the plurality of leads;
    displaying the determined delivery system score.

11. The method of claim 7, wherein lead score includes a summation of all of the fit score, the navigation score, and the stability score to suggest an optimal at least one lead.

12. A method to assist in identifying at least one of a lead or a delivery system of the lead to a target location, comprising:
    recalling image data including at least one dimension based on the image data;
    inputting a target location in the recalled image data;
    recalling with a processor system a lead catalogue having lead physical data relating to at least one selected lead;
    operating a processor system to execute a scoring program to determine a lead score based on at least one score of a fit score, a navigation score, and a stability score, for the at least one selected lead to be moved to and implanted at the target location, wherein the lead score is based on a comparison of the lead physical data of the at least one selected lead with a size of the input target location and a complexity of a path to the input target location;
    outputting the lead score for the at least one lead;

wherein the at least one lead is configured to be implanted at the target location.

13. The method of claim 12, wherein recalling with the processor system the lead catalogue having lead physical data relating to at least one lead, includes recalling with the processor system from a data storage system the lead catalogue having lead physical data relating to a plurality of leads;
wherein the lead physical data includes at least a diameter of the lead and at least one of a stiffness of the lead, a modulus of elasticity of the lead, a torquability of the lead, a distal tip geometry of the lead, a cant angle of the lead, or a steerability of the lead.

14. The method of claim 13, wherein operating the processor system to execute the scoring program to determine the lead score includes operating the processor system to execute the scoring program to determine a plurality of lead scores including at least one lead score for each lead of the plurality of leads.

15. The method of claim 14, wherein outputting the lead score for the at least one lead includes outputting the plurality of lead scores including at least one lead score for each lead of the plurality of leads.

16. The method of claim 14, further comprising:
determining a delivery system score by operating the processor system to execute the scoring program; and
outputting the delivery system score;
wherein the delivery system includes a guidewire or a catheter.

17. The method of claim 12, wherein inputting the target location includes selecting a location viewed in the recalled image data.

18. The method of claim 12, wherein operating the processor system to execute the scoring program to determine the lead score includes operating the processor system to:
execute the scoring program to:
determine a region of interference between an analyzed lead and a tortuosity of a vessel in the recalled image data including determining a number of curves of a path for the lead in the vessel to the target location and an angle of the curves lead in the vessel to the target location, and
compare the region of interference to a metric for an optimum lead, including weighting at least one of the fit score, the navigation score, or the stability score to determine the optimum lead.

19. A system to assist in identifying at least one of a lead or a delivery system of the lead to a target location in a subject, comprising:
a display device configured to display an image data of the subject;
an input system to input a target location in the displayed image data;
a data storage system having stored thereon a lead catalogue having lead physical data relating to at least one lead, wherein the lead physical data includes at least a diameter of the at least one lead and at least one of a stiffness, a modulus of elasticity, a torquability, a distal tip geometry, a cant angle, or a steerability of the at least one lead; and
a processor system configured to recall at least the lead catalogue and execute a scoring program to determine a lead score, based on the recalled lead catalogue, and includes at least one score of a fit score, a navigation score, and a stability score for the lead to be moved to and implanted at the target location, wherein the lead score is based on the lead physical data from the recalled lead catalogue of the at least one lead compared with a size of the input target location and a complexity of a path to the input target location;
wherein the display device is further configured to display the lead score for the at least one lead for viewing by a user;
wherein the at least one lead is configured to be implanted at the target location.

20. The system of claim 19, further comprising:
at least one cardiac lead that includes a physical property that relates to the lead physical data.

21. The system of claim 20, further comprising:
an implantable medical device configured to provide a treatment to the subject at the target location.

22. The system of claim 21, wherein the at least one cardiac lead includes a plurality of cardiac leads;
wherein the storage device includes the lead catalogue having lead physical data relating to each lead of the plurality of cardiac leads.

* * * * *